United States Patent [19]

Goulter et al.

[11] Patent Number: 5,797,890
[45] Date of Patent: Aug. 25, 1998

[54] SUPPORT DEVICES FOR RETAINING A MALE URINARY INCONTINENCE CONDOM CATHETER ONTO A PENIS

[75] Inventors: Victor H. Goulter; Barbara Goulter, both of San Francisco, Calif.

[73] Assignee: Goulter Medical Corporation, Portland, Oreg.

[21] Appl. No.: 597,179

[22] Filed: Feb. 6, 1996

[51] Int. Cl.⁶ .................................................. A61F 5/44
[52] U.S. Cl. ........................... 604/351; 604/352; 604/353
[58] Field of Search .................................. 604/349, 351, 604/353, 338, 352; 128/760, 842, 844; 4/144.1–144.4

[56] References Cited

U.S. PATENT DOCUMENTS

| | | | |
|---|---|---|---|
| 3,032,038 | 5/1962 | Swinn | 604/353 |
| 3,215,143 | 11/1965 | Wallenberg | 604/353 |
| 3,559,651 | 2/1971 | Moss | 604/349 |
| 4,713,067 | 12/1987 | Rothenberg et al. | 604/353 |
| 5,315,960 | 5/1994 | Lamp | 604/353 |

*Primary Examiner*—John G. Weiss
*Assistant Examiner*—David J. Cho
*Attorney, Agent, or Firm*—James J. Leary; Carol D. Titus

[57] ABSTRACT

A support strap whose lower end is sewn to a hook-and-loop band which encircles the sheath portion of a urine-collecting catheter and the user's penis. Its upper end has male part snaps sewn to it, which cooperate with female part snaps on the undergarment's waistband. The strap and band prevent the external urinary catheter from slipping off of the penis. The band has multiple indicating marks on the loop side and one mark on the hook side, for accurate repositioning of the band each time it is reapplied. A second embodiment has a front section of a garment onto which is sewn a grooved retainer ring, which encircles the penis. An applicator ring is used to spread the rim of the condom catheter to facilitate fitting the condom onto the penis and for fitting the rim into the groove of the grooved retaining ring.

12 Claims, 6 Drawing Sheets

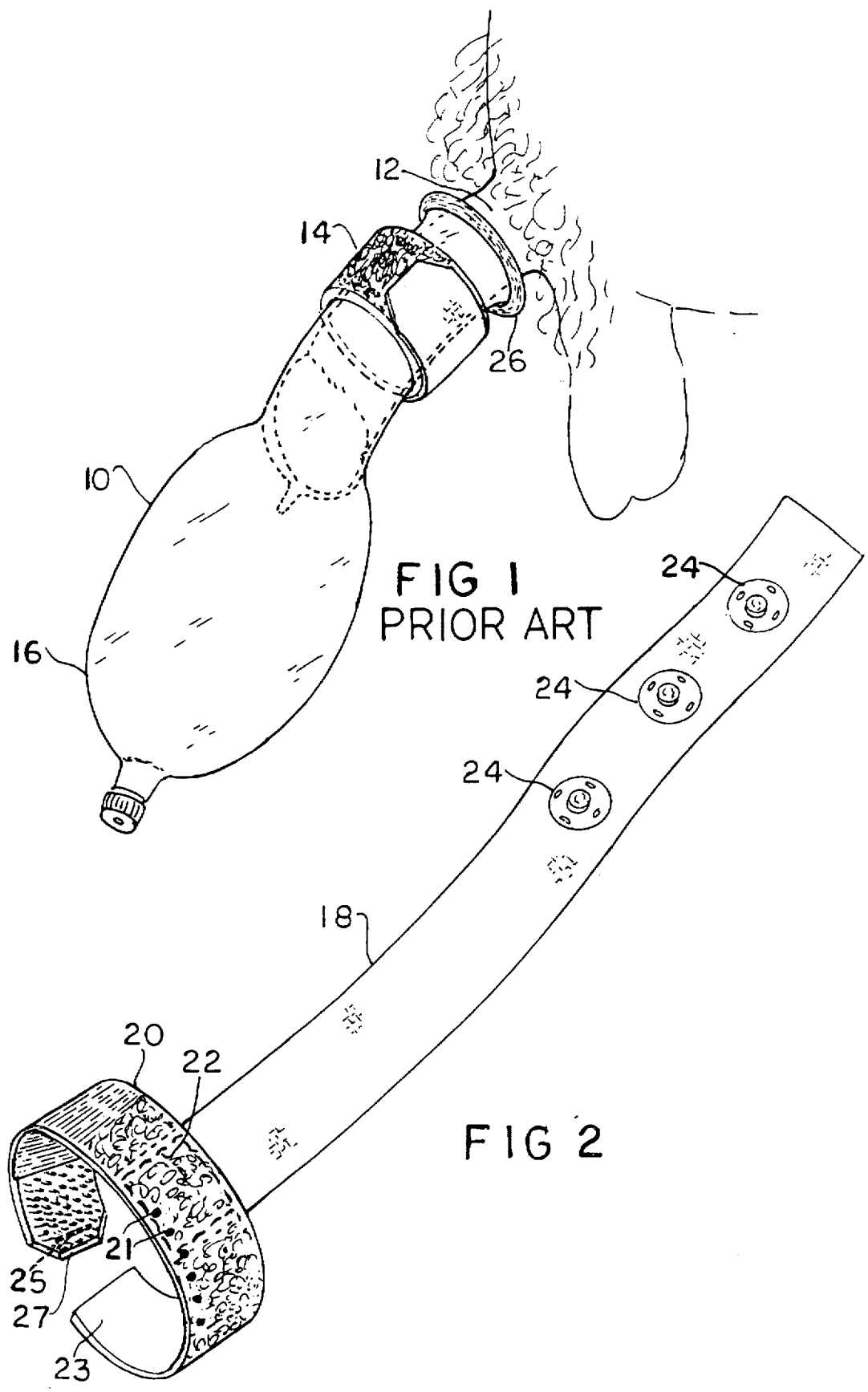

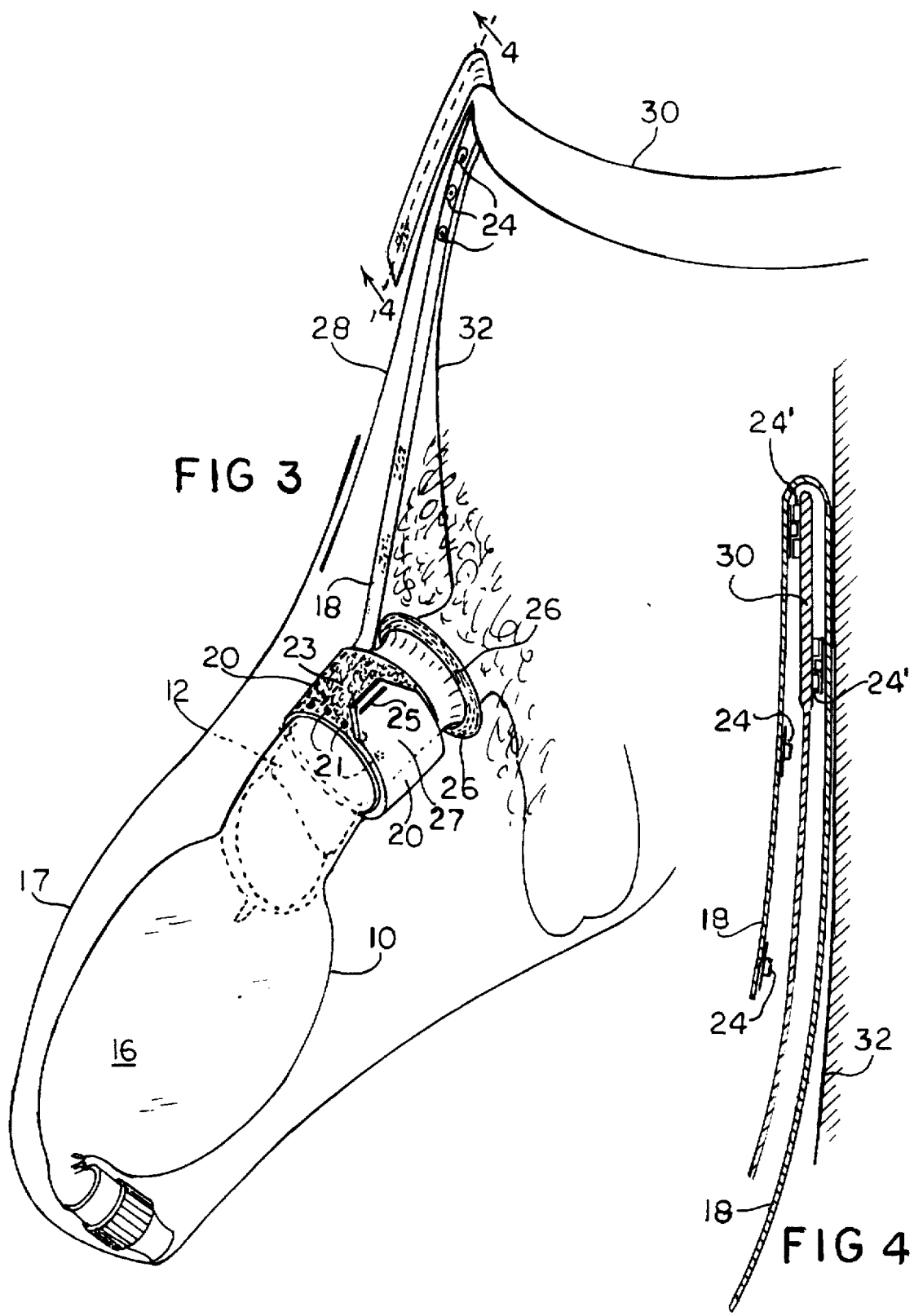

SUPPORT DEVICES FOR RETAINING A MALE URINARY INCONTINENCE CONDOM CATHETER ONTO A PENIS

BACKGROUND—FIELD OF INVENTION

The present invention relates to male urinary incontinence catheters, in particular to a more dependable means for retaining a catheter on the penis of a wearer without the use of adhesives.

BACKGROUND—FIELD OF INVENTION

Disclosure Document No. 385874 (dated Dec. 4, 1995), U.S. Pat. No. 5,009,649 (dated Apr. 23, 1991, issued to Victor Goulter and Barbara Goulter), U.S. Pat. No. 5,380,312 (dated Jan. 10, 1995, issued to Victor Goulter), and patent application Ser. No. 08/545,403 (filed Oct. 19, 1995), are incorporated by reference as part of the specification of this invention.

The first clinical trials, at the Shepherd Center of Atlanta, Ga., proved the safety, comfort and utility of the one piece Goulter Condom Catheter device, while defining its single weakness. The research team concluded that this catheter was superior to the control device in that it produced less incidence of skin breakdown and was easier to apply and use. It was also concluded that better adherence of the device should allow this product to outperform the control in many other areas as well.

G. D. Johnson in U.S. Pat. No. 4,971,071, dated Nov. 20, 1990 discloses an electrically conductive condom having a permanently attached retaining strap for securing about the person. The problem with this method is that it cannot be detached from the condom itself when quickly removing and refitting a new condom is required, and also requires the user to undress to reattach another condom.

P. E. Hogin in U.S. Pat. No. 4,354,494, dated Oct. 19, 1982 teaches an integrally formed strap for retaining a condom in place by stretching it around the user's scrotum. The problem with this method are many: firstly, the increasing weight of accumulating urine in a one-piece urinary incontinence catheter using this method would exert a pull on the scrotum, and quickly become unbearably uncomfortable; second, a thin strap as shown in the patent drawing would cut into the scrotum and add to the discomfort of the user, especially one who needs to wear it continuously; thirdly, this device was only intended for brief use, during coitus for contraceptive purposes.

The Applicants have been diligent, consistent and determined in seeking ways and means to prevent a catheter, especially their own of the above-mentioned patents issued and applied for, from slipping off the user.

In the past, the Applicants used such means as making the sheath snug-fitting, then increasing tension by using one or more elastic VELCRO bands around the sheath portion; also, having a series of fine circular grooves and raised relief ribs incised into the inner surface of the sheath portion of the catheter to improve grip; also, of attaching metal rings to the graspable rim of the sheath for hooking onto a harness or garment to be worn by the user.

All of the above means have been relatively successful in reducing the tendency of the catheter to slip, but none has been entirely reliable. The tendency to slip has remained somewhat dependent on such factors of the shape of the individual's penis; i.e., if the penis tapers toward the glans, the catheter is more likely to slip than if the glans is larger in diameter than the shaft. Slipping has also been affected by how tightly the VELCRO band has been adjusted to hold the device on the penis, creating a dilemma for some users, especially those with spinal injuries; bind the band too loosely and the catheter might slip; bind it too tightly and it might interfere with circulation.

Several other types of roll-on external catheters, such as those used with prior-art leg bags, make use of adhesives to hold the sheath in place. Adhesives, however, have several drawbacks. They not only fail to guarantee that the sheath will remain in place, but they often cause pain and sometimes injury while being removed. As a consequence, they are extremely unpopular with users.

Condom catheter slippage continues to be a major concern among nursing and care-giving staff, especially those attending the elderly, the spinal-injured and others likely to suffer male urinary incontinence. It is equally a worry to the otherwise able-bodied incontinent, who desire to continue normal activities and work.

Another problem applies to the use of elastic VELCRO (hook and loop) bands. These are fitted and adjusted by users and care-givers in a trial-and-error method to establish the proper amount of tension needed to hold the sheath comfortably yet firmly in place. Once the band has been removed however, the position is lost and must again be sought through trial and error next time it is applied.

OBJECTS AND ADVANTAGES

Accordingly, one object and advantage of the present invention is to provide a more positive means to prevent the catheter from slipping off the penis. Another object and advantage is to provide a means which can be fitted and/or removed easily and quickly. Another object and advantage is to provide a means which holds securely regardless of the shape of the penis.

Still another object and advantage is to provide a means which is simple and inexpensive to make. Another object and advantage is to provide a means that can be applied to very short, long, thick, thin, or retracted penises, regardless of shape or size. A still further object and advantage is to provide a means to retain catheters used by incapacitated and spinal injured patients and which cannot be readily pulled off by the senile or demented.

A further object and advantage is to provide a VELCRO hook and loop band that can be readily adjusted to a previously established and desired tension, without the need for repeated guesswork.

BRIEF DESCRIPTION OF DRAWINGS

FIG. 1 is a perspective view a penis fitted with a condom catheter of U.S. Pat. No. 5,380,312 which has been incorporated by reference and retained thereon with prior-art elastic VELCRO band.

FIG. 2 is a perspective view of a first embodiment of the present invention showing a combination of a support strap and an improved elastic VELCRO band, having a plurality of indicating marks thereon.

FIG. 3 is a perspective view of the support strap and VELCRO band combination of FIG. 2 attached to a penis.

FIG. 4 is an enlarged sectional view taken along line 4—4 of FIG. 3, illustrating snap buttons fitted to the support strap and undergarment's waistband.

3

Figure 6:
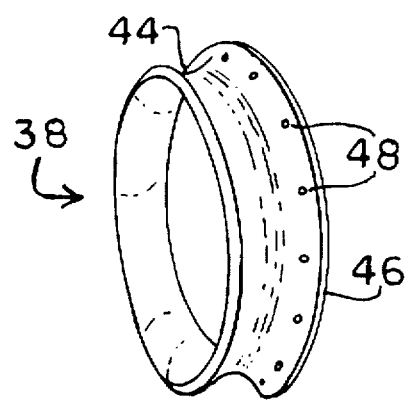

FIG. 6 is a perspective detailed view of a grooved retainer for attaching to a garment.

Figure 7:
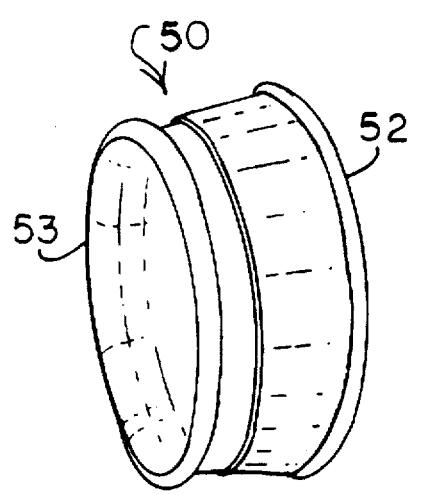

FIG. 7 is a perspective view of an improved applicator ring used in conjunction with a grooved retainer.

Figure 8:
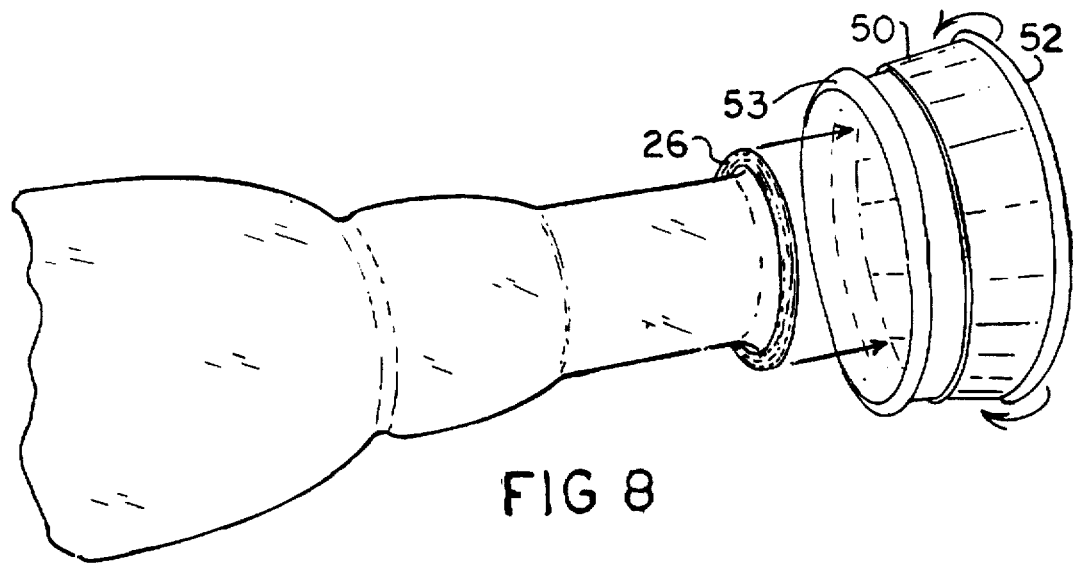

FIG. 8 is a perspective view of a catheter ready to be stretched onto an applicator ring.

Figure 9:
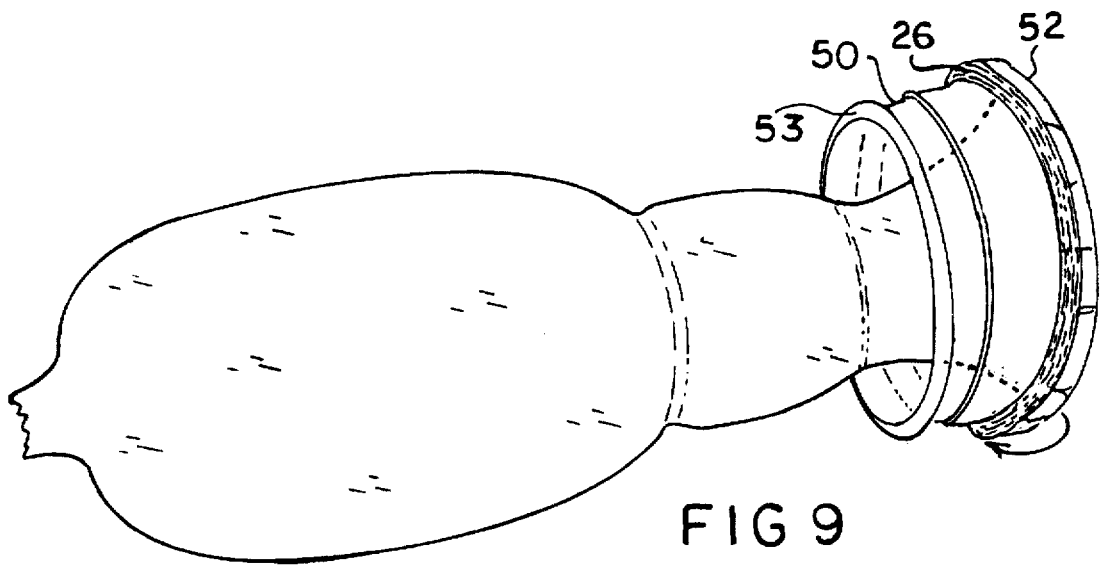

FIG. 9 is a perspective view of the catheter of FIG. 6 stretched around and over the end of an applicator ring.

Figure 10:
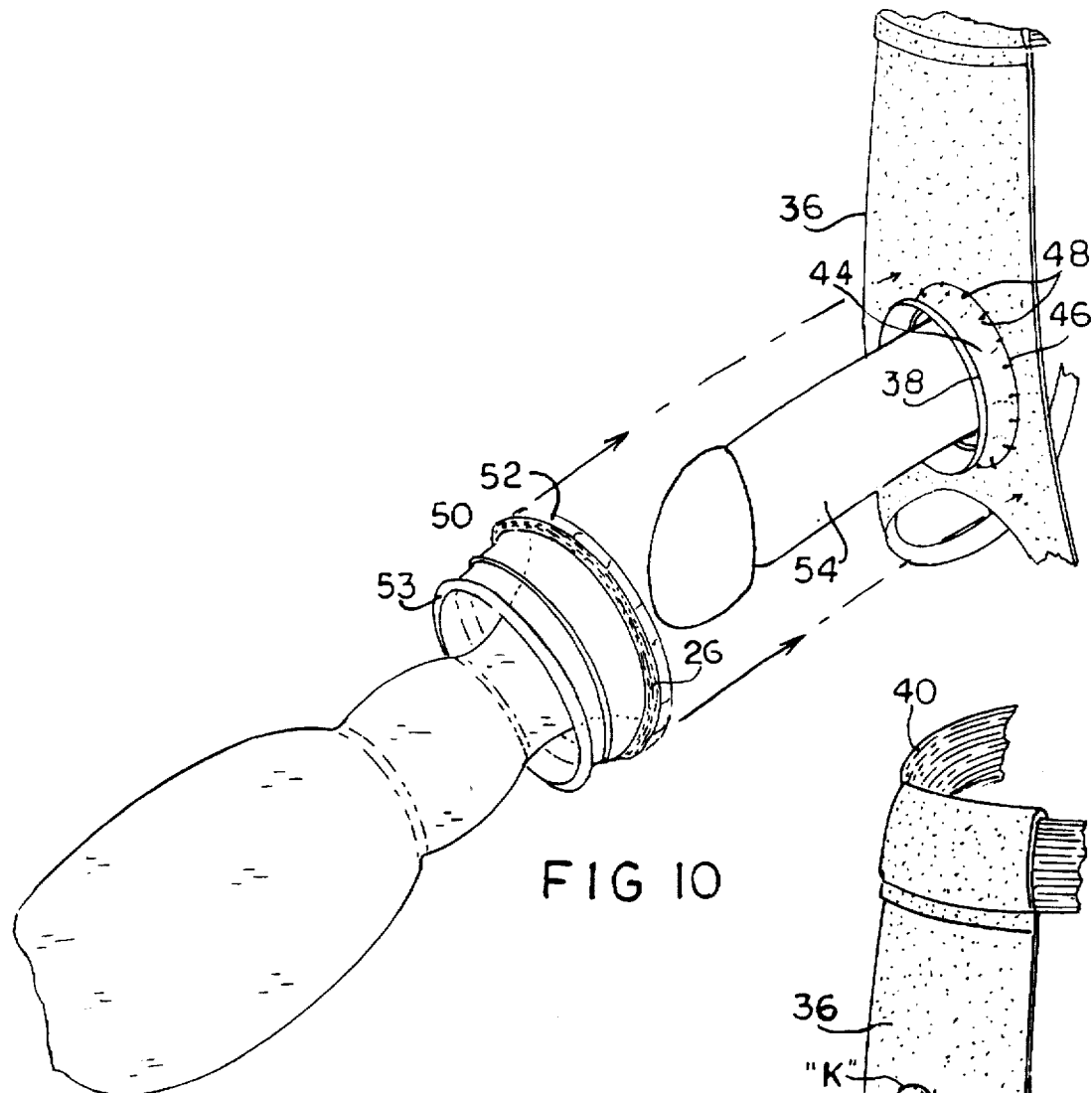

FIG. 10 is a perspective view of a garment including the grooved retainer encircling a penis, ready to receive a catheter with the use of an applicator ring.

Figure 11:
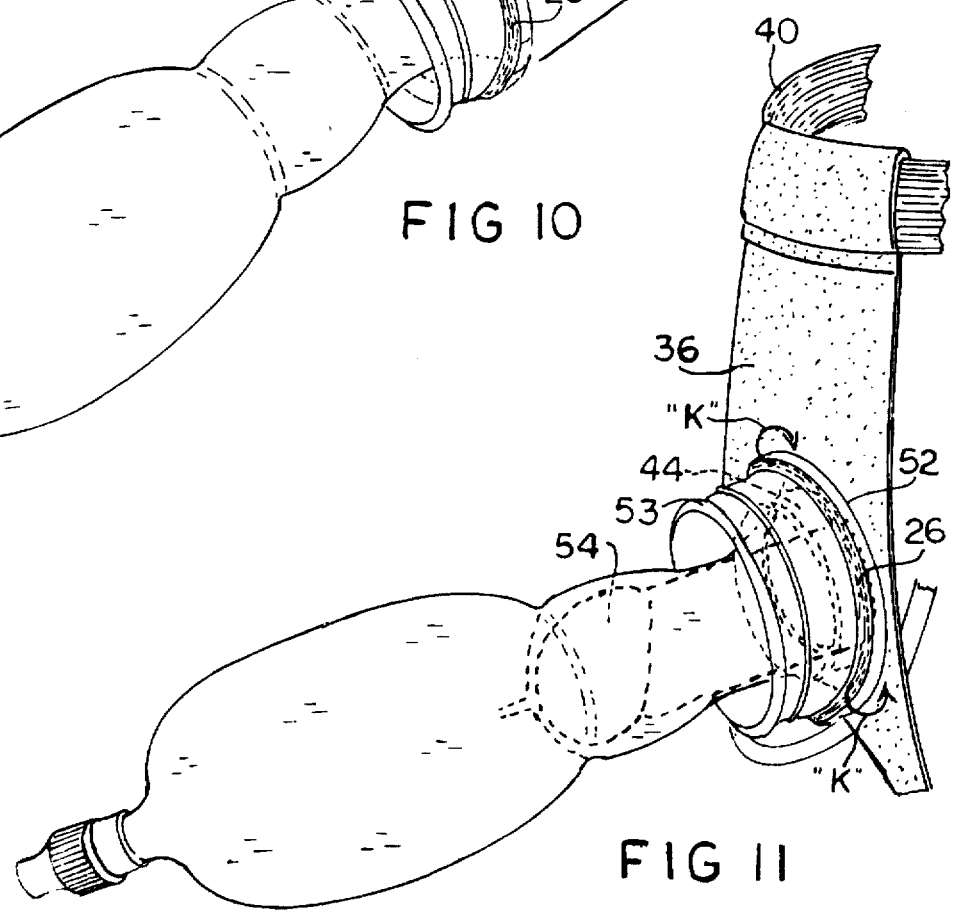

FIG. 11 is a perspective view of the catheter shown in FIG. 10, fitted as far as it will go onto a penis and in a position ready for dislodging graspable ring of the catheter into the grooved retainer on the undergarment.

Figure 12:
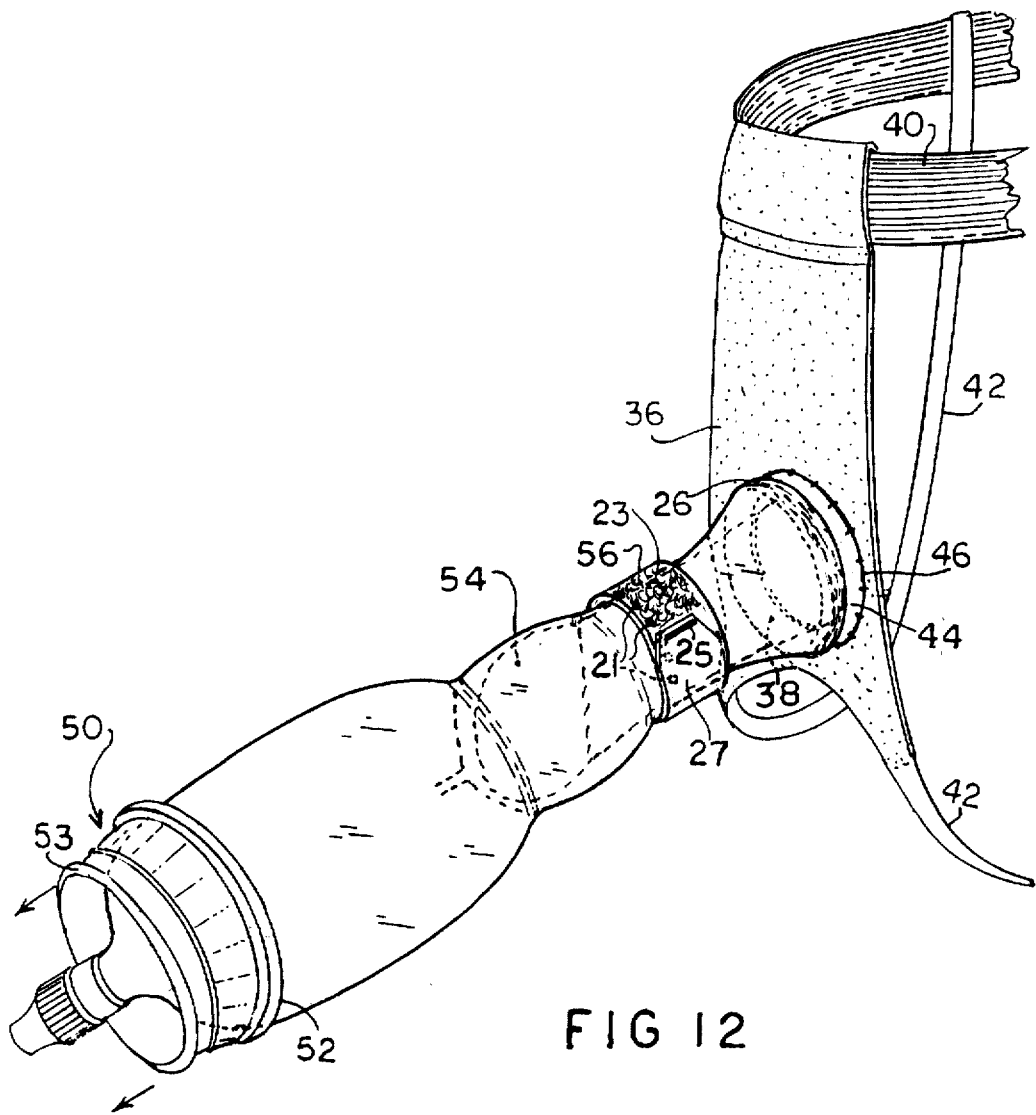

FIG. 12 is a perspective view of the catheter of FIG. 11, showing applicator ring removed entirely, and graspable ring securely dislodged off the applicator and into the circular groove of the retainer.

As shown, a VELCRO band having tension marks thereon may be fitted around the sheath portion of the catheter to enforce a seal.

DETAILED DESCRIPTION—FIGS 1–4

FIG. 1 shows a one-piece male urinary incontinence condom 10 of U.S. Pat. No. 5,380,312 which has been incorporated by reference, fitted onto a flaccid penis, 12. In previous embodiments, it is usually retained thereon by a prior-art elastic VELCRO band 14. The weight of voided urine which collects in the collection compartment 16 of condom 10 is supported by the extended pouch 17 of a modified undergarment shown in FIG. 3 in this application and also in FIG. 4 of our U.S. Pat. No. 5,009,649. However, since this embodiment was not always successful in keeping the Goulter condom catheter on tapering penises, the purpose of the present invention is hold the device in place more securely.

The present invention achieves this by the use of a support strap 18 (best seen in FIG. 2), which is combined with VELCRO band 20, preferably by sewing or otherwise securing strap 18 and band 20 together, as shown at 22 (FIG. 2). Support strap 18 has sufficient length to be attached to the waistband 30 (FIG. 3) of a modified undergarment by any suitable means, such as snaps or press studs or the like.

VELCRO band 20 (FIGS. 2 and 3) also shows a plurality of six indicating marks 21, permanently imprinted or otherwise made on loop section 23. Marks 21 are spaced about 5 mm (0.187") apart. A single cooperating mark 25 is made on hook section 27, such that when the user is fitting VELCRO band 20, mark 25 will align with, or near, one of the six marks 21, thus providing a visual read-out of where hook section mark corresponds relative to one of the loop section marks. Once the user has decided on the degree of tension and pressure most comfortable for himself, he can quickly achieve exactly the same fit each time he reuses the band in the future. If he feels it necessary to change the adjustment, he can note the change and use that as a future guide. The proper setting can be recorded by a care-giver as well, and also explained or directed to other care-givers; this would be especially useful in a nursing home setting, above all where incapacitated, helpless, senile or spinal-injured patients are treated.

It is recommended that our patented pouch-enlarged undergarment shown in FIG. 3 of this application and in FIG. 4 of our issued U.S. Pat. No. 5,009,649 be used with the condom catheter, and that snaps or similar adjustable anchoring means be attached to the waistband of said garment, to secure the support strap. The use of such a garment supports the device both from below, by pouch 17, and above, by support strap 18.

In order to conveniently and securely attach support strap 18 to modified undergarment's waistband 30, support strap 18 (FIGS. 2–4) is fitted with multiple male-part snaps, or press studs, 24, while one or two female-part snaps or press studs 24' are sewn to waistband 30 of the undergarment, such that while VELCRO band 20 is attached to a catheter at its lower end, the upper end is anchored to waistband 30 by the snaps, thereby positively securing condom 10 to penis 12 and preventing it from slipping off the penis.

It will also be realized that retention will no longer depend so heavily on pressure exerted by the VELCRO band. The band need only be sufficiently snug to form a seal and so that it will not slip back over the graspable ring 26, which is made integrally with the catheter during manufacture.

FIG. 4 shows a sectional view taken along broken line 4—4 of FIG. 3, showing portion of the user's body 32, portion of undergarment and its waistband 30 fitted with female-part snaps 25, and portion of support strap 18 fitted with male-part snaps 24'. Multiple fitting of male part snaps along the upper end of strap 18 allows for the adjustment of the length of strap 18 according to the height and body build of the user, so as to obtain the best length of strap in order to support catheter 10.

Alternatively, snaps can be replaced with buttons and button holes, hooks and eyes, VELCRO hook-and-loop portions; the support strap can even be secured to the waistband with a safety pin.

Support strap 18 can be made of any suitable non-elastic flexible fabric; it can also be made entirely or in part of elastomeric material, such as elastic bands or even latex strips. Testing has shown that fabric, elastic and combination support straps achieve similarly satisfactory results.

Support strap can also be attached to an elastic VELCRO band around a penis by a tab of hook-side VELCRO which can be sewn to the lower end of the strap. This method, however, carries the remote danger that the strap and the band may become separated; therefore, a positive attachment of strap and band (i.e., by sewing) is preferred.

In use, the weight of urine, as it accumulates in collecting compartment 16 of catheter 10, is supported both from beneath, by the undergarment pouch, and from above, by the tethered support strap and waistband. Together, they promote retention of the catheter irrespective of the penis' shape. Rather than pulling down on the wearer's penis, like most condom catheters currently available do, the Goulter condom catheter is so well supported that users have no sensation of wearing the device until the bulk of voided urine increases sufficiently to act as a reminder to drain the compartment. Draining, in turn, can be done by simply unzipping the trouser fly, pulling the end of the device out through the fly of the undergarment, and opening the release valve, making it possible for the wearer to use any convenient toilet or urinal.

SECOND EMBODIMENT—FIGS 5–12

Figure 5:
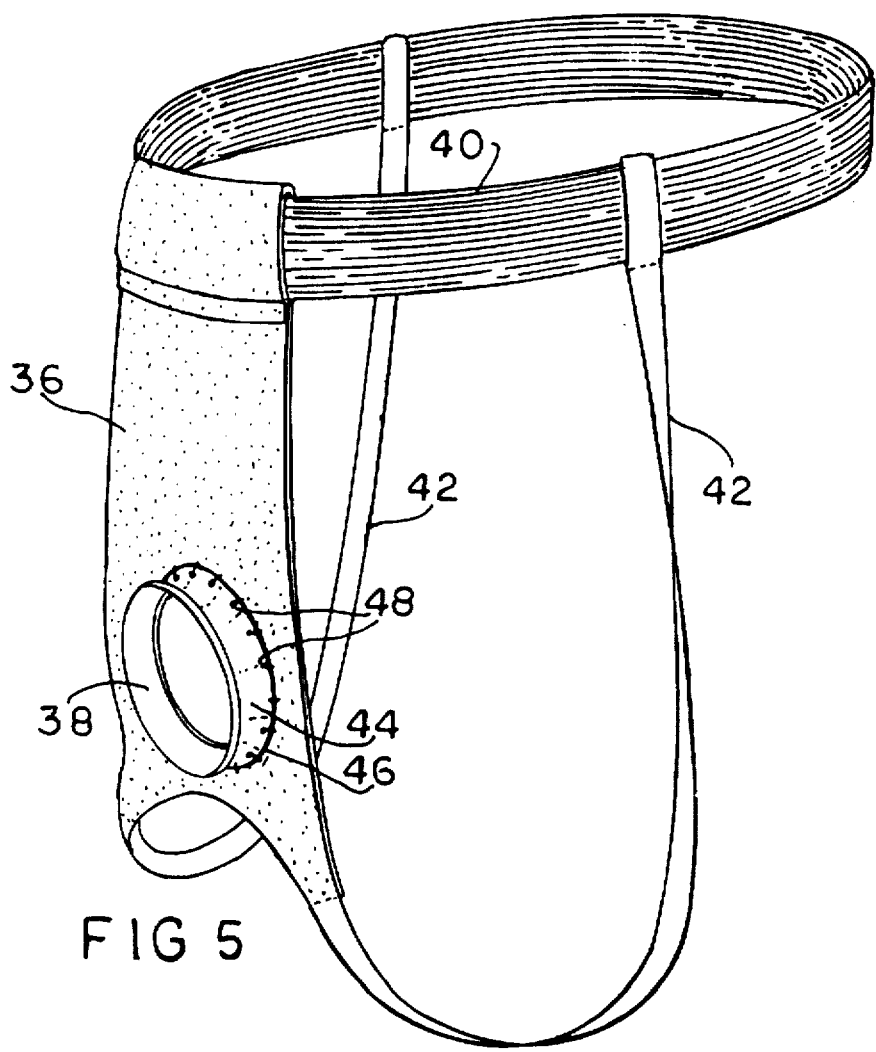
FIG. 5 is a perspective view of a second embodiment, comprising a retainer having a circular groove, which is attached to a garment to be worn by a user.

FIG. 5 shows a simple garment comprising a frontal section 36 incorporating a circular grooved retainer 38, an elastic waistband 40 at the top, and two leg straps 42 leading from the bottom of section 36 to the waistband at the side. Circular annular grooved retainer 38 (FIG. 6), hereafter called 'retainer,' can be made in two sizes, one larger in inner diameter than the thickness of most penises at the base and another of smaller diameter. Such retainers of whichever size, can be made of any suitable material, such as plastic, polyurethane, laminated wood, metal, fiber-glass, or any other skin-compatible suitable substance. The retainer has an outward facing circular groove 44, which protrudes forward of a mounting flange 46. Flange 46 is provided with multiple holes 48 for sewing flange 46 to frontal section 36 (FIG. 5). Frontal section 36 is preferably made of soft thick fabric, which acts as a protecting buffer between retainer 38 and the user's body.

Preferably, waistband 40 is made of wide elastic material in various waist sizes to suit individual users. It can also be made adjustable in size by known methods for individual users. Leg straps 42 can be made either of fabric or elastic material.

FIG. 7 shows an improved applicator ring 50, which is tapered, thus providing a large end 52 and a small end 53. Individual ends can be used effectively when fitting large and small size catheters onto penises and retainers.

FIG. 8 shows a catheter being fitted onto large size end 52 of an applicator ring, while FIG. 9 shows the graspable ring 26 of the catheter securely placed over large end 52, ready for fitting the catheter onto penis 54 as shown in FIG. 10.

FIG. 11 shows the catheter fitted as far as it will go onto penis 54 and large end 52 of applicator against front section 36 of the garment. In this position, graspable ring 26 is rolled off the end of the applicator ring and into groove 44 of the retainer in the direction of arrows "K".

FIG. 12 shows the catheter fitted onto penis 54, its graspable ring 26 securely locked and seated in annular groove 44. In this position the catheter is anchored securely to the garment and therefore cannot slip off the penis. The pressure applied between the sheath portion of the catheter and the penile shaft by the improved VELCRO band can be reapplied in the exact position to prevents the leakage of urine. It will be seen that mark 25 on the hook portion (FIG. 12) is aligned with the third mark 21 on the loop portion 27 of the band. Even too-large a catheter can be sealed against leakage by adding an elastic VELCRO band 56 attached around the sheath portion as shown in FIG. 12, tightened just sufficiently to effect a liquid tight seal.

Modified undergarment with enlarged pouch shown in FIG. 3 of this application and more clearly in our issued U.S. Pat. No. 5,009,649, herein incorporated by reference, is used in conjunction with the garment shown in FIG. 12 of this embodiment and is required for providing adequate support for the accumulation of urine collected in the condom catheter. This arrangement is suitable both for able-bodied users and bedridden patients.

SUMMARY, RAMIFICATIONS, AND SCOPE

Thus, the reader will see that the present invention has many advantages over prior art male incontinence devices. The non-disabled user enjoys freedom to engage in a normal life-style, including social and athletic activities such as working, swimming, aerobics, driving, running, skiing, dancing, or riding horses or motorcycles, without having to worry about the catheter coming off unexpectedly. He can dress in standard street clothing, knowing that his incontinence is imperceptible to all, even when he stands side by side with other men at a urinal. Patients and staff in hospitals can rest assured that the catheter will not come off until and unless purposely released from the retaining devices. Caregivers and users also will feel increased confidence in the use of elastic VELCRO straps due to the plurality of indicating marks relating to tightness of the band.

While the above description contains many specificities, the reader should not construe these as limitations on the scope of the invention, but merely as exemplifications of preferred embodiments thereof. Those skilled in the art will envision that many other possible variations are within its scope. For example, other forms of garments can be designed to attach the support strap; an anchoring patch can be adhesively attached to the bare skin of a user for attaching a support strap; or a waistband alone can be used to attach the support strap onto.

Accordingly, the reader is requested to determine the scope of the invention by the appended claims and their legal equivalents, and not by the examples which have been given.

We claim:

1. A combination of a device for retaining an external urinary catheter onto a penis of a wearer, said external urinary catheter having a proximal end for encircling the penis of the wearer and an undergarment having a waistband, said combination comprising:

an undergarment having a waistband to be worn about the wearer;

a band for encircling said proximal end of said external urinary catheter;

a support strap having a first end and a second end, said first end of said support strap being attached to said band;

and an adjustment means for adjusting the length of said support strap comprising a plurality of attachment means positioned at different positions along the length of said support strap, wherein said plurality of attachment means are attached to said second end of said support strap to said waistband of the undergarment having an expandable pouch for supporting said external urinary catheter.

2. The device of claim 1, wherein said band is made of an elastic material, and wherein said band fastens about said proximal end of said external urinary catheter with a hook and loop fastener.

3. The device of claim 1, wherein said band comprises a first end portion and a second end portion and an adjustable fastening means for connecting said first end portion to said second end portion in an overlapping manner, the degree of overlapping between said first end portion and said second end portion determining the tightness of said band around said proximal end of said external urinary catheter and the penis of the wearer, and wherein said band further comprises a plurality of indicating marks for indicating the degree of overlapping between said first end portion and said second end portion and therefore the tightness of said band around said proximal end of said external urinary catheter and the penis of the wearer.

4. The combination of claim 1, wherein said plurality of attachment means comprises removable attachment means selected from the group consists of snaps, press studs, safety pins, buttons, hooks and eyes, and hook and loop fasteners.

5. The combination of claim 1, wherein said band is made of an elastic material and, wherein said band fastens about said proximal end of said external urinary catheter with a hook and loop fastener.

6. The combination of claim 1, wherein said band further comprises an adjustable fastening means for fastening said band about said proximal end of said external urinary catheter.

7. A combination of a device for retaining an external urinary catheter onto a penis of a wearer, said external urinary catheter having a proximal end for encircling the penis of the wearer and an undergarment having a waistband, said combination comprising:

an undergarment having a waistband to be worn about the wearer;

a band for encircling said proximal end of said external urinary catheter;

a support strap having a first end and a second end, said first end of said support strap being attached to said band;

and an adjustment means for adjusting the length of said support strap comprising a plurality of attachment means positioned at different positions along the length of said support strap, wherein said plurality of attachment means are attached to said second end of said support strap to said waistband of the undergarment having an expandable pouch for supporting said external urinary catheter;

wherein said band further comprises a first end portion and a second end portion and an adjustable fastening means for connecting said first end portion to said second end portion and said second end portion determining the tightness of said band around said proximal end of said external urinary catheter and the penis of the wearer, and wherein said band further comprises a plurality of indicating marks for indicating the degree of overlapping between said first end portion and said second end portion and therefore the tightness of said band around said proximal end of said external urinary catheter and the penis of the wearer.

8. The combination of claim 7, wherein said adjustable fastening means for connecting said first end portion to said second end portion in an overlapping manner comprises a hook and loop fastener.

9. The combination of claim 7, wherein said band is made of an elastic material.

10. The combination of claim 7, wherein said band is made of an elastic material and wherein said adjustable fastening means for connecting said first end portion to said second end portion in an overlapping manner comprises a hook and loop fastener.

11. A combination of a device for retaining an external urinary catheter onto a penis of a wearer, said external urinary catheter having a proximal end for encircling the penis of the wearer and a distal end having a urine collecting compartment and an undergarment having a waistband, said combination consisting essentially of:

a band for encircling said proximal end of said external urinary catheter;

a single support strap having a first end and a second end, said first end of said single support strap being permanently attached to said band, said second end of said single support strap having at least one detachable attachment means, and;

an undergarment having a waistband to be worn about the wearer and having a pouch means for supporting said urine collecting compartment of said external urinary catheter, said undergarment having at least one corresponding detachable attachment means;

whereby said external urinary catheter is retained on the penis of the wearer by encircling said proximal end of said external urinary catheter with said band and attaching said at least one detachable attachment means of said single support strap to said at least one corresponding detachable attachment means of said undergarment.

12. The combination of claim 11, wherein said band comprises a first end portion and a second end portion of an adjustable fastening means for connecting said first end portion to said second end portion in an overlapping manner, the degree of overlapping between said first end portion and said second end portion determining the tightness of said band around said proximal end of said external urinary catheter and the penis of the wearer.

* * * * *